(12) United States Patent
Foster et al.

(10) Patent No.: US 8,822,207 B2
(45) Date of Patent: *Sep. 2, 2014

(54) CARTRIDGE FOR MEMS PARTICLE SORTING SYSTEM

(75) Inventors: John S. Foster, Santa Barbara, CA (US); Daryl W. Grummitt, Santa Barbara, CA (US); John C. Harley, Santa Barbara, CA (US); James P. Linton, San Diego, CA (US); Jaquelin K. Spong, Falls Church, VA (US)

(73) Assignees: Owl biomedical, Inc., Goleta, CA (US); Innovative Micro Technology, Goleta, CA (US)

( * ) Notice: Subject to any disclaimer, the term of this patent is extended or adjusted under 35 U.S.C. 154(b) by 341 days.

This patent is subject to a terminal disclaimer.

(21) Appl. No.: 13/374,899

(22) Filed: Jan. 23, 2012

(65) Prior Publication Data

US 2012/0190105 A1    Jul. 26, 2012

Related U.S. Application Data

(60) Provisional application No. 61/457,169, filed on Jan. 21, 2011.

(51) Int. Cl.

| C12M 1/36 | (2006.01) |
| C12M 1/38 | (2006.01) |
| C12M 3/00 | (2006.01) |
| B01L 3/00 | (2006.01) |
| G01N 15/14 | (2006.01) |
| C12M 1/00 | (2006.01) |
| B01L 7/00 | (2006.01) |

(52) U.S. Cl.
CPC .......... *C12M 47/04* (2013.01); *B01L 2400/043* (2013.01); *B01L 2200/0652* (2013.01); *B01L 2400/0439* (2013.01); *B01L 2400/0481* (2013.01); *B01L 3/502761* (2013.01); *B01L 2300/0816* (2013.01); *B01L 2400/0478* (2013.01); *B01L 7/52* (2013.01); *G01N 15/1459* (2013.01); *G01N 2015/149* (2013.01)
USPC ............. 435/288.5; 435/288.7; 435/288.4; 435/288.3; 435/305.1; 435/305.2

(58) Field of Classification Search
CPC ............. B01L 3/502761; B01L 2400/0481; B01L 7/52; B01L 2200/0652; G01N 2015/149
USPC .......... 435/288.7, 288.3, 288.4, 288.5, 305.1, 435/305.2
See application file for complete search history.

(56) References Cited

U.S. PATENT DOCUMENTS

| 6,838,056 B2 | 1/2005 | Foster |
| 7,220,594 B2 | 5/2007 | Foster et al. |
| 7,229,838 B2 | 6/2007 | Foster et al. |
| 7,264,972 B2 | 9/2007 | Foster |
| 2005/0105077 A1* | 5/2005 | Padmanabhan et al. ........ 356/39 |
| 2005/0173313 A1 | 8/2005 | Tyvoli et al. |

(Continued)

*Primary Examiner* — Nathan Bowers
(74) *Attorney, Agent, or Firm* — Jaquelin K. Spong

(57) ABSTRACT

A disposable cartridge is described which is compatible with a MEMS particle sorting device. The disposable cartridge may include passageways which connect fluid reservoirs in the cartridge with corresponding microfluidic passageways on the MEMS chip. A flexible gasket may prevent leakages and allow the fluid to cross the gasket barrier through a plurality of holes in the gasket. Vents and septums may also be included to allow air to escape and fluids to be inserted by hypodermic needle. A MEMS-based particle sorting system using the disposable cartridge is also described.

20 Claims, 5 Drawing Sheets

(56) References Cited

U.S. PATENT DOCUMENTS

| | | |
|---|---|---|
| 2006/0269446 A1 | 11/2006 | Gilbert et al. |
| 2007/0178529 A1* | 8/2007 | Breidford et al. .............. 435/7.1 |
| 2008/0050283 A1* | 2/2008 | Chou et al. ................... 422/101 |
| 2009/0084946 A1 | 4/2009 | Zhu et al. |
| 2009/0322830 A1 | 12/2009 | Smith et al. |
| 2010/0206731 A1 | 8/2010 | Lau et al. |
| 2010/0304429 A1 | 12/2010 | Butler et al. |
| 2012/0009619 A1* | 1/2012 | Gilbert et al. ................... 435/29 |

* cited by examiner

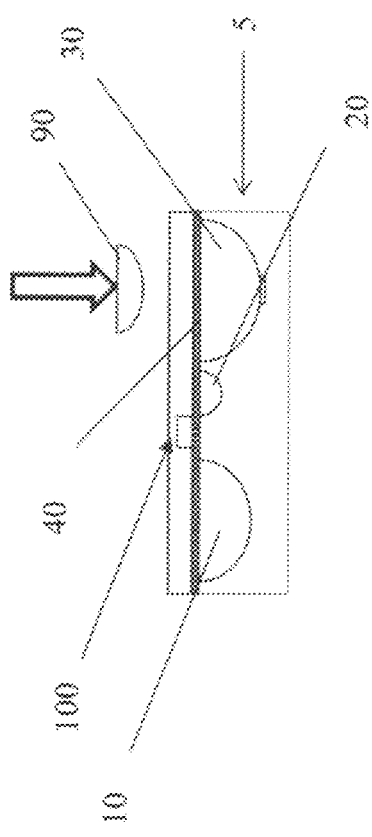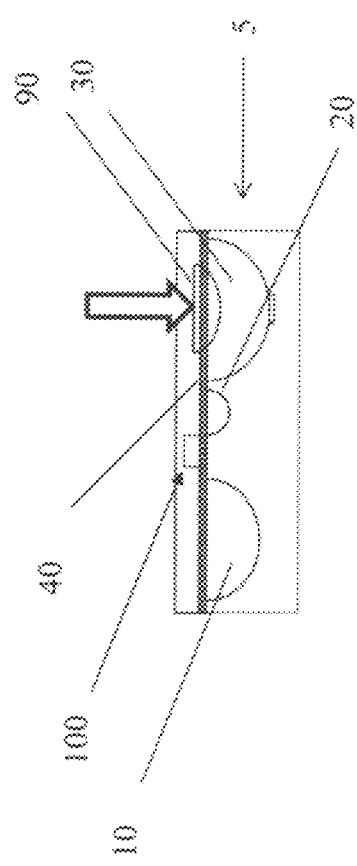
Fig. 4a
Fig. 4b

CARTRIDGE FOR MEMS PARTICLE SORTING SYSTEM

CROSS REFERENCE TO RELATED APPLICATIONS

This application claims priority to U.S. Provisional Application No. 61/457,170, filed Jan. 21, 2011 and incorporated by reference herein in its entirety. This application is related to U.S. patent application Ser. No. 13/374,899 filed on Jan. 23, 2012.

STATEMENT REGARDING FEDERALLY SPONSORED RESEARCH

Not applicable.

STATEMENT REGARDING MICROFICHE APPENDIX

Not applicable.

BACKGROUND

This invention relates to a system and method for sorting small particles in a fluid stream with a MEMS device.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for the moveable switch may be thermal, piezoelectric, electrostatic, or magnetic, for example.

MEMS devices, in the form of a movable valve, may be used as a sorting mechanism for sorting various particles, such as cells from a fluid stream such as blood. The particles may be transported to the sorting device within the fluid stream enclosed in a microchannel, which flows under pressure. Upon reaching the MEMS sorting device, the sorting device directs the particles of interest to a separate receptacle, and directs the remainder of the fluid stream to a waste receptacle.

A number of patents have been granted which are directed to such MEMS-based particle sorting devices. For example, U.S. Pat. No. 6,838,056 (the '056 patent) is directed to a MEMS-based cell sorting device, U.S. Pat. No. 7,264,972 b1 (the '972 patent) is directed to a micromechanical actuator for a MEMS-based cell sorting device. U.S. Pat. No. 7,220,594 (the '594 patent) is directed to optical structures fabricated with a MEMS cell sorting apparatus, and U.S. Pat. No. 7,229,838 (the '838 patent) is directed to an actuation mechanism for operating a MEMS-based particle sorting system. Each of these patents is hereby incorporated by reference, and each is assigned to Innovative Micro Technology, assignee of the present invention.

MEMS-based cell sorter systems may have substantial advantages over existing fluorescence-activated cell sorting systems (FACS) known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from a nozzle, the droplets are separated into different bins electrostatically, based on the fluorescence signal from the tag. Among the issues with these systems are cell damage or loss of functionality due to the decompression, difficult and costly sterilization procedures between sample, inability to sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

SUMMARY

A system and method are described for separating particles of interest from the remainder of a fluid stream using a MEMS device. The system may make use of a unique micromechanical MEMS actuator which may improve the speed, simplicity and manufacturability of the particle sorting system. The MEMS actuator may be housed in a unique, disposable, self-contained cartridge which also houses a sample reservoir, a sorted reservoir, and waste reservoir, as well as the fluidic pathways between these reservoirs.

A particle sorting system based on this cartridge and MEMS actuator is described. In contrast to existing FACS flow cytometers, the MEMS-based cell sorter does not rely on a sheath fluid, and does not atomize the droplets containing the target cells. As a result, the MEMS-based cell sorting system can sort rare cells such as cancer cells or tumor cells, sperm cells, or other particles with outstanding speed and precision, and a very high proportion of the cells (>95%) are viable after sorting. The system is small, inexpensive and requires virtually no sterilization as the components in contact with the sample fluid are discarded after use.

The disposable cartridge may include at least one microfabricated particle sorting structure formed on a substrate and installed in the substantially sealed, disposable cartridge, a quantity of biocompatible material with a plurality of fluid reservoirs disposed therein, with one or more fluidic passageways formed between the microfabricated particle sorting structure and the reservoirs, and a flexible gasket covering the reservoirs, wherein a plurality of holes formed in the gasket allows a fluid flow to between at least one of the reservoirs and the microfabricated particle sorting structure.

A system and method are described for separating particles of interest from the remainder of a fluid stream. The system may make use of a unique micromechanical actuator in the aforementioned disposable cartridge. The disposable cartridge improves the speed, simplicity, cost and manufacturability of the particle sorting system, and completely encloses the sample stream. Because the cartridge is discarded between samples, no re-sterilization of the system is required.

These and other features and advantages are described in, or are apparent from, the following detailed description.

BRIEF DESCRIPTION OF THE DRAWINGS

Various exemplary details are described with reference to the following figures, wherein:

FIGS. 4a and 4b are schematic views of one embodiment of a pumping mechanism for forcing fluid through the disposable cartridge and MEMS actuator.

DETAILED DESCRIPTION

The system described herein is a MEMS based particle sorting system which may make use of a unique, self-contained disposable cartridge which houses a MEMS chip and actuator on board the cartridge. The MEMS actuator design may improve the speed, precision, cost and manufacturability of the system, compared to prior art systems, and is further described in co-pending U.S. patent application Ser. No. 13/374,898 filed on Jan. 23, 2012, filed on an even date herewith, and incorporated by reference in its entirety. Use of the disposable, self-contained cartridge allows the system to remain uncontaminated by the sample fluid, and thus no sterilization of the system is needed. These features enable an inexpensive high performance cell sorting system, designed around the MEMS actuator and disposable cartridge, which includes a detector, a force-generating apparatus, and various optical inspection equipment on board in the system.

In the figures discussed below, similar reference numbers are intended to refer to similar structures, and the structures are illustrated at various levels of detail to give a clear view of the important features of this novel device.

Figure 1:
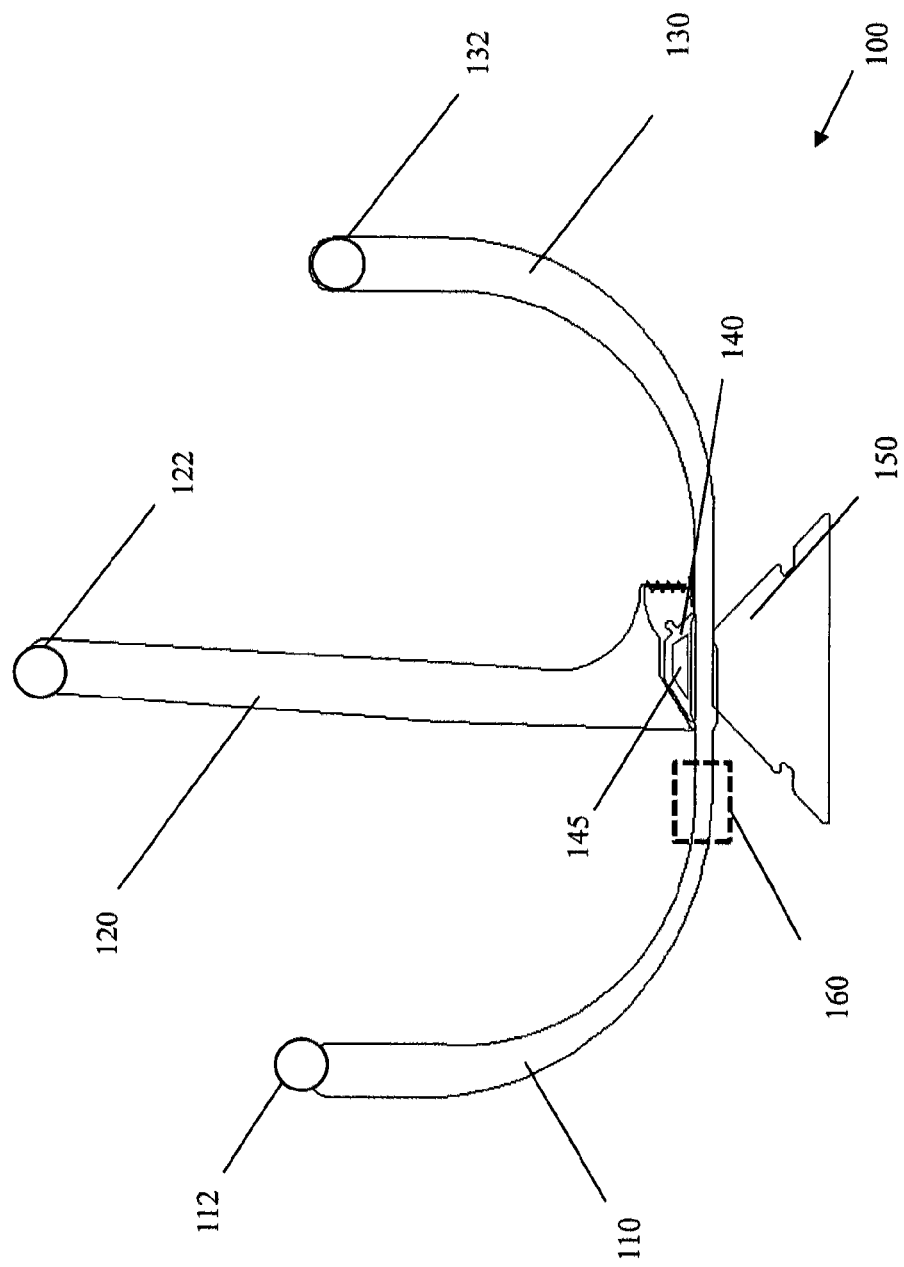
FIG. 1 is a simplified illustration of the MEMS actuator in the MEMS particle sorting system.

FIG. 1 is a schematic illustration of the MEMS particle sorting actuator, which is usable in the MEMS particle sorting system described below. The area designated 100 refers to a portion of a semiconductor substrate that includes a microfabricated device, that is, area 100 is a semiconductor chip containing the microfabricated sorting mechanism. The substrate or chip 100 also defines a plane in which the microdevice is fabricated, as well as the plane in which the microdevice moves. The motion and fabrication plane is generally parallel to the surface of the substrate 100, and in the plane of the paper.

The substrate or chip 100 may also include a plurality of small fluidic channels 110, 120 and 130 formed in the substrate 100. The fluidic channels allow a fluid sample stream to flow therein, wherein the fluid stream may contain a multitude of particles, some of which are to be separated from the others, forming a purified sample at the output. The channels may include an input channel 110 which admits the sample fluid from an input via hole 112 in substrate 100, a sort channel 120 which directs the sorted target particles into sort output via hole 122 and on to sort reservoir 20 contained in the cartridge (see FIG. 3), and a waste channel 130 which allows all the non-target particles to flow through the device to be routed through a waste via hole or port 132 to be collected in a waste reservoir 30, also contained in the cartridge (See FIG. 3). Examples of target particles may include stem cells, cancer cells, bacteria, blood cells, sperm cells, lymphocytes, T-cells, for example. The fluid stream may be blood, lymph, semen, saline or dilute samples of these fluids, for example. The substrate or chip 100 may be covered by an optically transparent, flat layer which encloses the fluidic channels 110, 120 and 130, while allowing light to pass through this layer.

While in the fluid stream, the components of the sample may pass through a detection region 160, and past the movable structure 140 of the MEMS actuator, which either diverts the stream into the sort channel 120 and to port 122, or allows it to pass to the waste channel 130 and port 132. The chip 100 may include areas 145 and 150 in the MEMS actuator into which a magnetically permeable material has been inlaid, whose function is described more fully below.

In the detection region 160, the target particle may be distinguished from the other constituents of the fluid sample. The detection means may be, but is not necessarily, a microfabricated structure located in the input channel 120 upstream of the movable structure 140, and generally in detection region 160. The detection means may be based on any number of characteristics or attributes that distinguish the target particle from the others in the fluid stream. For example, the particles may be distinguished by, for example, differences in an electrical attribute, a hydrodynamic attribute, a magnetic attribute, an optical attribute, a thermal attribute, mass, and a mechanical attribute of the particle, to name just a few. This list is not meant to be exhaustive, but instead to provide examples of detection systems which may be used with the actuator described herein.

In one embodiment, the target particle may be a particular cell which may be tagged with a fluorescent tag, which emits light of a particular color when irradiated by a laser at a particular wavelength. Such tags are well known in the field and include for example fluorescein, Texas Red, phycobiliproteins, cyanine derivatives and rhodamine. While much of this disclosure is directed to this application, it should be understood that the systems and methods described herein are also applicable to other detection mechanisms used to distinguish particles one from another. These mechanisms may be well known, or may yet be invented.

Upon passing through the detection region 160, a signal is generated by the detector (not shown) indicating that a target particle is present in the detection region 160. After a known delay, a signal is generated by a controller which indicates that the sorting gate, i.e. the movable structure 140, is to be opened, in order to separate the target particle which was detected, from the other components in the fluid stream. Both the flap-like movable structure 140 and the fixed feature 150 may comprise permeable magnetic materials, so that a magnetic force may arise between them when a magnetic field is present. When the signal is generated by the controller, a force is generated between the embedded magnetically permeable material 145 in the flap-like movable structure 140 and a fixed feature 150, which draws the flap-like movable structure 140 towards the fixed feature 150. This motion closes off waste channel 130 and waste port 132, and redirects the target particle into a sort channel 120 and sort port 122 at the end of sort channel 120. The sorted sample is subsequently collected from a sort reservoir in the disposable cartridge which holds the sorted sample.

In particular, the signal generated by the detector indicates that a force-generating mechanism is to be activated. This force-generating mechanism may be a current-carrying coil and a permeable magnetic core, which resides in the cell sorting system and is more fully described with respect to FIG. 5, below. Accordingly, the force-generating structure is a separate mechanism that is not directly, mechanically coupled to the movable structure 140, the MEMS actuator 100 or the disposable cartridge 5. Upon receiving the signal that the target particle has been detected, a current may be applied to the coil, generating a magnetic field in the permeable core. This field is shaped by the fixed feature 150 in order to provide a region with a high density of flux lines in the vicinity of the fixed feature 150. As is well known from elementary magnetostatics, the permeability portion 145 of movable structure 140 may be drawn toward regions of increasing flux density, and therefore may be drawn toward fixed feature 150, closing the waste channel 130 and opening the sort channel 120. The details of this sorting mechanism are described in greater detail in co-pending U.S. patent application Ser. No. 13/374,898 filed on Jan. 23, 2012, filed on an even date herewith, and incorporated by reference in its entirety.

Figure 2:
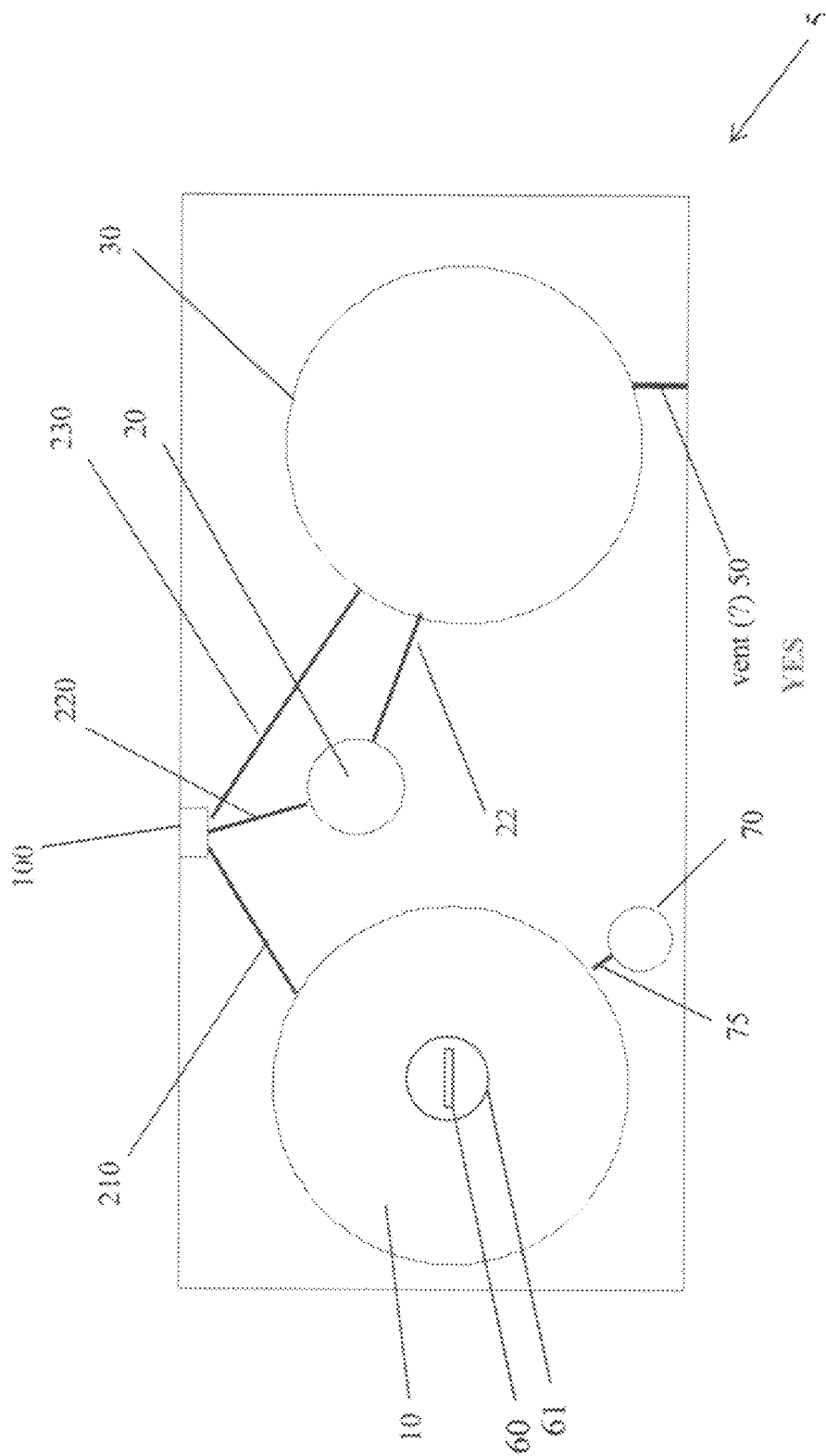
FIG. 2 is a simplified plan view of a first embodiment of the MEMS actuator disposed in the disposable cartridge.

FIG. 2 is a simplified illustration of the MEMS actuator chip 100 disposed in the disposable cartridge 5. The cartridge may be made of a quantity of a biocompatible material such as polycarbonate or poly methyl methacrylate (PMMA), or even metal. Preferably, this material is also sterilizable and moldable. The cartridge body may be machined, or injection molded from the biocompatible material, for example. Preferably, this quantity of biocompatible material may be transparent, allowing the position of the MEMS chip 100, as well as the sample reservoirs 10, 20 and 30 to be viewed from outside the cartridge 5.

As mentioned above, the cartridge material may be optically transparent, allowing viewing of both the MEMS chip 100 from above, and the fluid reservoirs from below. The ability to view the MEMS chip 100 may enable better alignment of the cartridge with respect to the detection system and force-generating mechanism, both of which may reside in the cell sorting system shown in FIG. 5. The word "cartridge" should be understood to mean a container holding a quantity of fluid and designed for insertion into a mechanism, in this case, the MEMS particle sorting system. The cartridge is hereafter described as "self-contained," which should be understood to mean that the cartridge may be handled as a complete unit, it may be inserted or withdrawn from the particle sorting system in its entirety, and that the sample fluid, sorted fluid and waste fluid are completely contained within the cartridge at all times. "Substantially sealed" should be understood to mean that once the fluids are introduced to the cartridge, the fluid flows entirely within the cartridge, although one or more vents in the fluid reservoirs may allow gas exchange with the external environment. "Disposable" should be understood to mean that the cartridge may be easily withdrawn from the particle sorting system, and replaced with another like cartridge. After use, the disposable cartridge may be discarded, or it may be used to store the sample for a longer period of time, for example, in a freezer. This becomes a significant cost advantage in terms of the cost of the cartridge and the cost of operation of the particle sorting system, described further below, because the more expensive components may reside in the cell sorting system and be reused.

The cartridge 5 may have reservoirs for sample 10, waste 30 and the sorted effluent 20. Each of the reservoirs may be connected to the MEMS chip 100 by a small passageway 210, 220 and 230 in the plastic of the cartridge, and is connected to the corresponding microfluidic channels 110, 120 and 130 in the chip 100. For example, passageway 220 may connect sort reservoir 20 with the sort channel 120 in MEMS chip 100 by way of via hole 122 in substrate 100. Passageway 230 may connect waste reservoir 30 with the waste channel 130 in MEMS chip 100. Passageway 210 may connect input sample reservoir 10 with the input channel 110 in MEMS chip 100. The actual connection between these passageways may be accomplished by a flexible gasket, as described further below.

As mentioned above, the disposable cartridge 5 may be equipped with a flexible gasket. This gasket may have several functions: it may provide a fluid seal to the passageways; it may also allow the fluid to traverse the gasket through a set of holes in the gasket; and it may provide a flexible membrane for applying pressure to the input reservoir and causing the fluid sample to flow. This pressurization method is described in greater detail below with respect to FIGS. 4a and 4b below.

The cartridge 5 may also be equipped with a flexible fill septum 70 which allows the sample fluid to be introduced to the sample reservoir 10 with a hypodermic needle into the septum, for example. In particular, a hypodermic needle may be inserted into the septum 70, the plunger depressed, and fluid from the hypodermic chamber is forced into the sorting reservoir 10 through a narrow passage 75 in the plastic. This may prevent the sample fluid from exiting the input sample reservoir via this route when under pressurization, rather than through passageway 210.

The input reservoir may also be equipped with a magnetic stir bar 60 which may be confined in a depression or chamber 61 formed with the input reservoir 10. The magnet 60 may interact with a rotating magnetic field in the cell sorting system described below, in order to agitate or mix the components of the fluid sample, or to maintain the components in suspension.

The cartridge 5 may also be equipped with a vent 50 which allows gas to escape from the waste reservoir 30 as it is displaced by fluid pumped from the input reservoir 10. This vent may reduce the pressure required on the input reservoir 10 in order to cause the sample fluid to be completely transferred from the input reservoir 10, through the MEMS chip 100, and into either the sort reservoir 20 or the waste reservoir 30. The vent 50 may also contain a micropore filter (not shown), which creates a barrier to particles or bacteria entering the cartridge 5, and may thus help maintain the sterility of the cartridge 5. A vent 22 may also be used to connect reservoir 20 and reservoir 30, to reduce the pressure in reservoir 20. This vent 22 may include a filter such that cells or other particles of interest cannot pass between reservoirs 20 and 30. Alternatively, vent 22 can be routed directly out of the disposable cartridge in like manner as vent 50.

Figure 3:
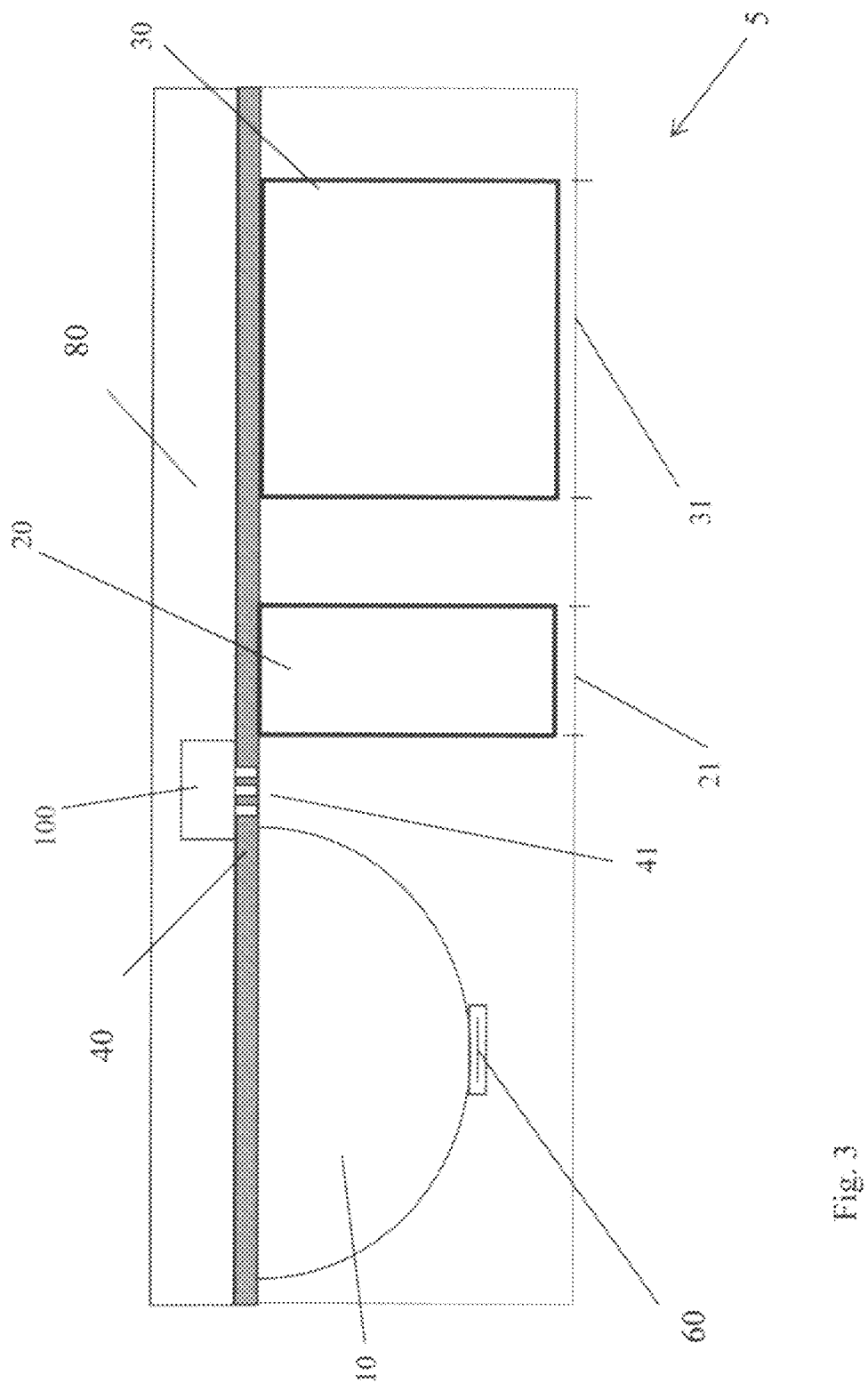
FIG. 3 is simplified cross sectional view of the cartridge shown schematically in FIG. 2, showing the flexible gasket.

FIG. 3 is a cross sectional diagram of the disposable cartridge 5 showing the flexible gasket 40, a plurality of gasket through holes 41, along with the profiles of the input reservoir 10, sort reservoir 20 and waste reservoir 30. The gasket 40 may provide a fluid seal to the passageways 110, 120 and 130, and may include a plurality of channels 41 through which the fluid in passageways 210, 220 and 230 reach the MEMS chip 100 and microfluidic channels 110, 120 and 130 by way of via holes 112, 122 and 132 in substrate 100. The flexible gasket may also form a flexible membrane over the input reservoir, allowing a piston applied thereto to force the fluid from the input reservoir to through passageway 210 and to MEMS chip 100, and to movable sorting structure 140 via input channel 110. The gasket may be formed of a biocompatible, flexible material such as silicone, which may be stamped or molded into the desired outline. The gasket may be less than about 500 microns thick, in order to provide a sufficiently flexible yet robust membrane.

A clear, plastic lid 80 may secure the MEMS chip 100 in the disposable cartridge 5, and may secure the flexible gasket 40 to the cartridge base. The plastic lid 80 may simply be glued or cemented to the flexible gasket 40, after alignment of the plurality of through holes 41 to the plurality of passageways 110, 120 and 130. Using a clear material for the cartridge lid 80 allows the condition of the MEMS chip 100 to be seen from above, so as to align the position of the MEMS chip 100, or the MEMS chip 100 may be viewed through the clear base material. This may allow alignment of the movable structure 140 and detection region 160 with respect to the detector and force-generating apparatus.

Another important feature of the disposable cartridge 5 is the cross sectional profile of the input reservoir 10, the sorted reservoir 20 and the waste reservoir 30, as shown in FIG. 3. The input reservoir 10 may have a curved or hemispherical floor as shown, whereas the sort reservoir 20 and waste reservoir 30 may have rectangular cross sectional profiles. The curved or hemispherical spherical profile of the input reservoir may make it consistent with the piston fluidic drive, as explained in greater detail with respect to FIGS. 4a and 4b below. The rectangular profile of the sort reservoir 20 and waste reservoir 30 may have a flat floor, which allows their contents to be viewed from below. This capability may be convenient for assessing the quality and condition of the sort effluent and waste effluent. One viewing area 21 may be provided for the sort reservoir 20, and another viewing area may be provided for the waste reservoir. For cartridge designs which do not use optically transparent materials, these viewing areas may be optically transparent windows in the opaque cartridge materials which may be uncovered when viewed, and otherwise covered with an opaque shutter or other covering.

In particular, an optical imaging system may be placed beneath the disposable cartridge 5, either when the cartridge is in the cell sorting system or when it has been withdrawn. When withdrawn, the disposable cartridge 5 may simply be placed on a microscope stage and the contents of the sort reservoir 20 and waste reservoir 30 may be imaged and inspected. This may be a valuable feature in obtaining a rough estimate of the effectiveness or success of a particular sorting run. The contents of the reservoirs need not be withdrawn to allow this inspection.

FIGS. 4a and 4b are a schematic illustration of the propulsion system which may be used to force the sample fluid through the input passageway 210 and channel 110 to the MEMS chip 100 and then out through the sort channel 120 to sort reservoir 20 (if a target particle) or waste channel 130 and waste reservoir 30 (if another component). The propulsion system may include a shaped piston or plunger 90, which has approximately the same contour as the input sample reservoir 10. For example, if the input sample reservoir has a spherical shape, the piston or plunger 90 may have a similar spherical shape of smaller radius. This allows the piston or plunger to deflect the flexible gasket 40 onto the surface of the fluid pool in the input reservoir, creating a pumping pressure which forces the fluid through the input passageway 210 to the input channel 110, to the detection region 160, past the movable structure 140 and into either the sort channel 120, sort passageway 220 and sort reservoir 20, or the waste channel 130, waste passageway 230 and waste reservoir. From the sort reservoir 20, the sorted sample may be retrieved by a hypodermic needle through another septum, or otherwise unloaded from the disposable cartridge 5 for further processing or analysis.

In other embodiments, the pressure against the membrane or gasket may be applied by providing baric pressure in a pressure chamber, rather than by a plunger or piston 90.

FIG. 4a shows the disposable cartridge in relation to the piston 90 before the pressure is applied from the piston 90 to the gasket 40. This may be the position of the piston 90 during the loading or unloading of the cartridge 5 into the cell sorting system, which is described below with respect to FIG. 5, which shows the complete system. In FIG. 4b, the piston 90 is lowered into contact with the flexible gasket 40, applying a pressure to the surface of the fluid. This pressure forces the fluid through the input passageway 110, through the MEMS chip 100, and then to the sort reservoir 20 or the waste reservoir 30.

Figure 5:
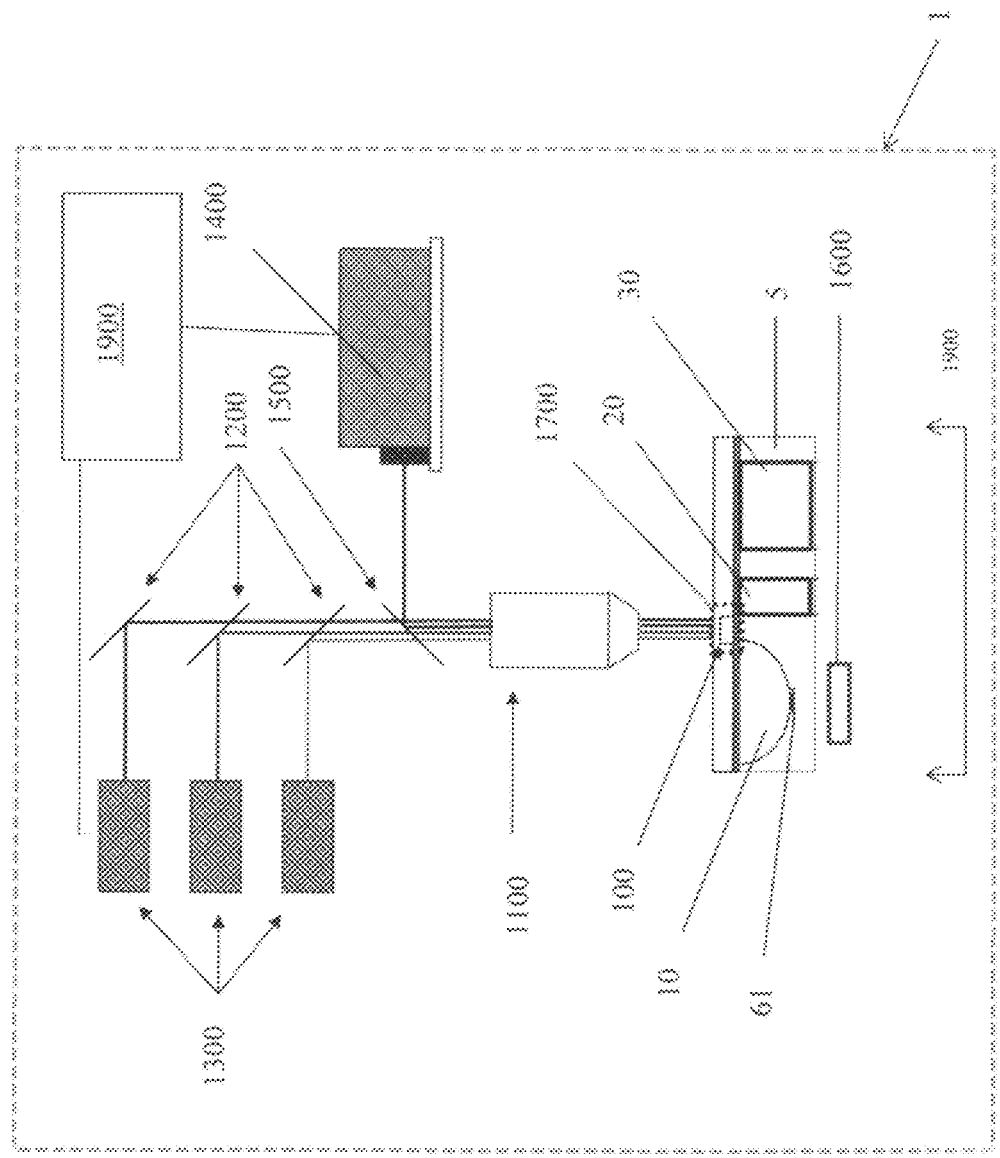
FIG. 5 is a schematic view of the disposable cartridge and MEMS actuator in a particle sorting system with an optical detectors for detecting tagged particles.

FIG. 5 is a more detailed illustration of one embodiment of a particle sorting system 1 using the microfabricated flap valve movable structure 140 and MEMS chip 100 in the disposable cartridge 5. Reference number 5 refers to the disposable, self-contained cartridge 5 described above that houses a sample reservoir 10, a sort reservoir 20 and waste reservoir 30, which are in fluid communication with input channel 110, sort channel 120 and waste channel 130 shown in FIG. 1. The MEMS chip 100 containing the MEMS actuator 140 may be disposed in the front of this cartridge 5 as shown in FIG. 3. This cartridge 5 may be disposed in the system such that a laser and detector are situated directly adjacent to and above the detection region 160 shown in FIGS. 1 and 2.

In one embodiment, the target particle may be a particular cell, such as a stem cell, or a cancer cell, which has been tagged with a fluorescent marker. This marker emits photons having a particular energy when irradiated with a laser operating at a predefined wavelength. Accordingly, in this cell sorting system, a laser source 1400 may be directed by a turning mirror 1500 through the detection optics 1100 onto the MEMS chip 100 in the detection region 160 shown in FIG. 1. The optical axis of the detection optics 1100 and the laser source 1400 may be collinear, at least over a portion of the optical path. Thus, the orientation of the laser application and optical detection along this optical axis may be perpendicular or orthogonal to the substrate fabrication plane, orthogonal to the plane of motion of the sorter flap movable structure 140 and orthogonal to the flow of the sample fluid through the detection region. This may have important consequences as the light traverses the surfaces with an orthogonal angle of incidence, which may reduce specular reflection and thus reduce or eliminate a noise source in the detection scheme.

The fluorescence emitted from the irradiated particles may be shaped by detection optics 1100 and separated by dichroic mirrors 1200 and directed into a bank of photodetectors 1300. A plurality of photodetectors may accommodate multiple wavelengths of emitted light, for multiparametric detection. The signal output by the photodetectors 1300 indicates the presence or absence of the target particle in the detection region 160. The signal may be delivered to a controller 1900, which manages the relative timing of the components in the particle sorting system 1, and collects the data. The controller 1900 may be a general purpose computer or a specialized circuit or ASIC. Upon detection of the target particle, a signal is generated by the controller 1900 which energizes the force-generating or flux-generating apparatus 1700. The force generating apparatus is a device which causes a force to arise in the movable structure itself, causing the motion of the movable structure toward the force-generating apparatus, which has an equal and opposite force arise therein. In general, this force-generating apparatus is not directly mechanically coupled to the movable structure 140. For example, the force-generating apparatus 1700 may be a source of magnetic flux which causes a magnetostatic force to arise in the permeable material 145 of the movable structure. This force pulls the flap or movable structure toward the force-generating apparatus 1700, opening the sort channel 120 and port 122 to the flow and closing the waste channel 130 and waste port 132. Importantly, the force-generating apparatus 1700 resides in the particle sorting system 1, rather than in the disposable cartridge 5. As mentioned previously, this may reduce the cost and complexity of the disposable cartridge 5.

As mentioned, in one embodiment, this force-generating apparatus 1700 is a source of magnetic flux, for example an electromagnet, which is energized to produce a magnetic flux from a current-carrying coil. The flap or movable structure 140 is also formed substantially from a permeable magnetic material, such as nickel-iron permalloy, which is drawn toward the gradient of this magnetic flux as is well known from elementary magnetostatics. This force pulls the flap or movable structure 140 toward the force-generating apparatus 1700, redirecting the target particle from the input channel 110 to the sort channel 120.

Shown only schematically because it is behind and obscured by the disposable cartridge 5 is the force-generating apparatus 1700, for example, a magnetic core with a wound coil. As mentioned previously, upon receiving the appropriate signal from one of more photodetectors 1300 indicating that a target particle is present in the detection region 160, a controller 1900 may energize the coil, producing a magnetic field which is shaped by the fixed features 150 in the vicinity of the movable structure 140. The permeable magnetic inlay 145 of the permeable structure is drawn toward the fixed feature 150, opening the sort channel 120 and closing the waste channel 130. By this means, the target particle is separated from the other components of the fluid stream and collected in the sort reservoir 20 in the disposable cartridge 5.

Also included in the cell sorting system 1 may be a mechanism which generates a rotating magnetic field 1600. This rotating field may simply be a rotating permanent magnet or a rotating coil. This rotating field may interact with bar magnetic stirrer 60, causing it to rotate in the magnet chamber 61, and mix the contents of the input reservoir 10 in which the magnet 60 is housed.

The disposable cartridge 5 may be inserted into a housing containing the components shown in FIG. 5. The insertion area may be a stage with mechanisms available for fine positioning of the disposable cartridge 5 against one or more data, which orient and position the detection region and movable structure 140 with respect to the collection optics 1100 and the force-generating apparatus 1700. If finer positioning is required, the input stage may also be a translation stage, which adjusts the positioning based on observation of the location of the movable structure 140 relative to the datum. This observation may be made through the optically transparent lid 80 or the quantity of transparent biocompatible material of the cartridge 5, as described above.

The MEMS cell sorting system 1 shown in FIG. 5 may also be equipped with a number of accessories. For example, accessory 2000 may be a vibration-generating mechanism, mechanically coupled to the disposable cartridge 5. This vibration-generating mechanism may be, for example, and ultrasound transducer, an audio speaker, a piezoelectric transducer, or the like, which is capable of applying a transitory pressure wave or acoustic vibration to the fluid in the disposable cartridge. This pressure wave or acoustic vibration may help in dispersing clots or coagulations, which are well known in association with biological and cellular materials. Adherent particles such as platelets and DNA fragments are often difficult to handle, especially given the small dimensions of the microfabricated particle sorting structure shown in FIG. 1. The vibration-generating mechanism may apply the acoustic power at any number of convenient points, for example, to the stage holding the disposable cartridge as shown in FIG. 5, or to the piston 90 in contact with the flexible gasket 40. Because of the modular architecture of the MEMS particle sorting system shown in FIG. 5, such accessories are relatively straightforward to implement.

In another embodiment, accessory 2000 may be a heating or refrigeration stage on which the disposable cartridge 5 is mounted. The heating or refrigeration stage may be thermally coupled to the disposable cartridge. It is well known that lowering the temperature of various biological materials may slow their metabolic processes, and thereby extend their lifetime and/or functionality. Spermatozoa are notoriously sensitive to temperature, for example. By using such a refrigeration stage, the sample fluid may be cooled throughout the sorting process, thereby increasing the viable proportion of the sorted effluent. Alternatively, applying heat to the disposable cartridge may speed up metabolic processes or catalyze other thermally activated processes. It should be understood that these accessories are optional and motivated by the requirements of the application, and are not required to practice this invention.

Thus, the MEMS particle sorting system may be used in conjunction with a MEMS chip 100 and a compact, disposable, biocompatible cartridge 5, and optionally, various accessories. Among the unique details of this cartridge design are:

1. May consist of moldable, biocompatible material
2. May contain fluidic channels used to connect chambers to sorting device
3. May contain a flexible gasket between the channels and the sorting device
4. May contain venting channels to allow air to escape the chambers
5. Venting channels may contain small pore filters to maintain sterility
6. May have viewable (via camera or microscope) sorted and un-sorted output chambers
7. Input chamber may be sealed via gasket, septum or sterile filter
8. Fluid chamber may be driven via pressurization (either mechanical or baric)
9. Filling area may use a septum to prevent leakage and allow hypodermic sample loading
10. Input chamber may house stir bar for sample mixing Any and all of the aforementioned MEMS actuators may be fabricated by deep reactive ion etching the appropriate pattern in the active (device) layer of a silicon-on-insulator (SOI) substrate, after formation of the magnetizable portions of the microactuators. The silicon-in-insulator substrate may include a 625 um silicon "handle" wafer, coated with a 1 um thick layer of silicon dioxide, followed by a 50 um "active" or "device" silicon layer. Details regarding the manufacturing and assembly processes of devices similar to these structures may be found in the incorporated '056, '972, '594 and '838 patents, and are outlined briefly below.

The magnetizable portions of the microactuators may first be made by depositing a thin metallic seed layer, such as chromium (Cr) and gold (Au) and depositing photoresist over the seed layer. The photoresist may then be patterned according to the shapes of the magnetizable features 145-945 and 150-950 of microactuators 140-940. Finally, a magnetically permeable material with high saturation magnetization such as NiFe permalloy (70-80% Ni, 30-20% Fe) may be plated onto the patterned photoresist and seed layer, forming the magnetically permeable structures. The photoresist and non-plated portions of the seed layer may then be removed, and the structure planarized by chemical mechanical polishing. An etch mask may subsequently cover the permalloy structures to avoid etching them during the formation of the remainder of the micromechanical actuator using deep reactive ion etching, for example, as described in the aforementioned '056 patent.

The movable structures may then be etched into the "device" layer of the SOI wafer. Deep reactive ion etching may form vertical walls needed to precisely define the shape of the movable structure. After etching the movable structure, it may be released from the thicker handle layer by etching the insulating layer beneath the movable structure. At this point, the movable structure is free to move relative to the handle layer. The fluidic channels may then be enclosed by glueing a flat, optical cover to the SOI wafer to form a wafer assembly.

The wafer assembly can then be diced to form the individual devices. These devices may then be installed in a sort system cartridge as described above.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A substantially sealed, disposable cartridge for a MEMS particle sorting system, comprising:
    at least one microfabricated particle sorting structure formed on a substrate and installed in the substantially sealed, disposable cartridge;
    a quantity of biocompatible material with a plurality of fluid reservoirs disposed therein, with one or more fluidic passageways connecting the fluid reservoirs to the MEMS particle sorting system;
    a flexible gasket covering the reservoirs, wherein a plurality of holes formed in the gasket allows a fluid to flow between at least one of the reservoirs and the microfabricated particle sorting structure,
    wherein the microfabricated particle sorting structure is fabricated on a layer of a substrate, and includes:
    a plurality of microfabricated fluidic channels formed in a plane of the layer of the substrate; and
    a movable structure formed in and from the layer of the substrate with a motion substantially in the plane, acted on by a magnetic force substantially in the same plane and wherein the movable structure simultaneously opens a first microfabricated fluidic channel which is in the plane and closes a second microfabricated fluidic channel also in the plane wherein the motion is substantially rotary, and the movable structure is attached to the substrate at one or more fixed points, and further comprising one or more flexible springs attached to the one or more fixed points, which return the movable structure to a first position when the force is removed.

2. The substantially sealed, disposable cartridge of claim 1, further comprising:
    a sample fluid disposed in a sample reservoir;
    a sample input passageway upstream of the microfabricated particle sorting structure, a sort passageway and a waste passageway downstream of the microfabricated particle sorting structure, which are in fluid communication with the sample reservoir, the microfabricated particle sorting structure, a sort reservoir and a waste reservoir,
    wherein the microfabricated particle sorting structure diverts a target particle from the sample passageway to the sort passageway and blocks the waste passageway when the target particle is detected, and
    wherein the sort passageway, sort reservoir, waste passageway and waste reservoir are all formed in the substantially sealed, disposable cartridge.

3. The substantially sealed, disposable cartridge of claim 2, further comprising:
    at least one vent formed in the biocompatible material which permits a gas to pass from at least one of the reservoirs to an environment external to the substantially sealed, disposable cartridge.

4. The substantially sealed, disposable cartridge of claim 2, further comprising:
    a lid affixed to the gasket to seal the gasket against the quantity of biocompatible material and against the substrate, and wherein the gasket is disposed against the quantity of biocompatible material on one side of the gasket, and the lid and substrate on another side of the gasket.

5. The substantially sealed, disposable cartridge of claim 2, further comprising:
    a flexible sample input septum associated with the sample reservoir; and
    a magnetic stir bar disposed at the bottom of the sample reservoir.

6. The substantially sealed, disposable cartridge of claim 5, wherein the input septum is in fluid communication with the sample reservoir by a fluid channel linking the input septum with the sample reservoir.

7. The substantially sealed, disposable cartridge of claim 2, further comprising:
    at least one transparent viewing window disposed at the bottom of at least one of the sort reservoir and the waste reservoir.

8. The substantially sealed, disposable cartridge of claim 2, further comprising:
    a detection region in the input passageway, wherein as the sample fluid flows through the detection region, a signal is obtained from the sample fluid which distinguishes a target particle from the other components of the sample fluid, wherein this signal is based on at least one of an electrical attribute, a hydrodynamic attribute, a magnetic attribute, mass, an optical attribute, a thermal attribute, and a mechanical attribute of the particle.

9. The substantially sealed, disposable cartridge of claim 2, wherein
    the microfabricated particle sorting structure includes-a movable structure which pivots around at least one fixed point, wherein each of the fixed points is located on the same side of an axis of motion of the movable structure, and wherein the movable structure opens a sort channel to divert the target particle into the sort channel when the movable structure pivots about the at least one fixed point.

10. The substantially sealed, disposable cartridge of claim 2, wherein the sample reservoir has a curved floor forming the bottom of the input reservoir; and wherein the sort reservoir and waste reservoirs each have a substantially rectangular cross section with a flat floor.

11. The substantially sealed, disposable cartridge of claim 9, further comprising:
    at least one transparent viewing window at the bottom of at least one of the sort reservoir and the waste reservoir, allowing the contents of at least one of the sort reservoir and the waste reservoir to be viewed from below the respective reservoirs.

12. A MEMS particle sorting system, comprising:
    the substantially sealed, disposable cartridge of claim 1; and
    a detector which detects a target particle passing in a sample fluid flowing through a detection region in the microfabricated particle sorting structure.

13. The MEMS particle sorting system of claim 12, further comprising:
    a laser whose output is directed onto the detection region of the microfabricated particle sorting structure, wherein the laser light impinges orthogonally on the detection region and the sample fluid flowing therethrough.

14. The MEMS particle sorting system of claim 12, further comprising:

an optical axis oriented orthogonally to a plane of the substrate, the detection region and the flow therethrough;
at least one turning mirror which redirects the output of the laser onto the optical axis;
at least one optical detector; and
at least one dichroic minor disposed on the optical axis which redirects fluorescent light from the detection region into the at least one optical detector.

15. The MEMS particle sorting system of claim 14, further comprising:
a force-generating apparatus which induces motion in the microfabricated particle sorting structure toward the force-generating apparatus, without being mechanically coupled to the microfabricated particle sorting structure.

16. The MEMS particle sorting system of claim 14, further comprising:
a controller which receives a signal from the at least one optical detector, and outputs a signal to the force-generating apparatus, activating the force-generating apparatus to move the microfabricated particle sorting structure.

17. The MEMS particle sorting system of claim 14 further comprising:
a piston which exerts a pressure on the flexible gasket, forcing a fluid to move from one of the fluid reservoirs to the microfabricated particle sorting structure, to another of the fluid reservoirs under the pressure from the piston.

18. The MEMS particle sorting system of claim 14, further comprising:
a vibration-generating mechanism which is mechanically coupled to at least one of the flexible gasket and the biocompatible material, that applies a transient pressure wave to the sample fluid in the fluidic passageways.

19. The MEMS particle sorting system of claim 14, further comprising:
at least one of refrigeration and heating apparatus which is thermally coupled to the disposable cartridge, that cools or heats the sample fluid in the disposable cartridge.

20. The MEMS particle sorting system of claim 14, further comprising:
a mechanism which generates a rotating magnetic field, which may interact with a magnetic stirrer in the substantially sealed, disposable cartridge, to mix the sample fluid.

* * * * *